(12) United States Patent
Solomon

(10) Patent No.: US 7,374,421 B2
(45) Date of Patent: May 20, 2008

(54) SYSTEM AND METHOD FOR IMPROVED CONTROL OF TOOTH MOVEMENT WITH ELASTIC REPOSITIONING APPLIANCES

(76) Inventor: Frederick Solomon, 64 Central St., Byfield, MA (US) 01922

(*) Notice: Subject to any disclaimer, the term of this patent is extended or adjusted under 35 U.S.C. 154(b) by 0 days.

(21) Appl. No.: 11/391,635

(22) Filed: Mar. 28, 2006

(65) Prior Publication Data
US 2006/0223022 A1    Oct. 5, 2006

Related U.S. Application Data

(60) Provisional application No. 60/666,908, filed on Mar. 31, 2005.

(51) Int. Cl.
*A61C 3/00* (2006.01)
(52) U.S. Cl. ............... 433/18; 433/24; 433/2
(58) Field of Classification Search ............ 433/2, 433/6, 18, 24
See application file for complete search history.

(56) References Cited

U.S. PATENT DOCUMENTS

| | | | |
|---|---|---|---|
| 2,467,432 A | 4/1949 | Kesling |
| 3,178,820 A | 4/1965 | Kesling |
| 3,407,500 A | 10/1968 | Kesling |
| 3,510,946 A | 5/1970 | Kesling |
| 3,683,502 A | 8/1972 | Wallshein |
| 3,724,075 A | 4/1973 | Kesling |
| 3,837,081 A | 9/1974 | Kesling |
| 3,950,851 A | 4/1976 | Bergersen |
| 4,195,046 A | 3/1980 | Kesling |
| 4,253,828 A | 3/1981 | Coles et al. |
| 4,370,129 A | 1/1983 | Huge |
| 4,504,225 A | 3/1985 | Yoshii |
| 4,505,673 A | 3/1985 | Yoshii |
| 4,591,341 A | 5/1986 | Andrews |
| 4,609,349 A | 9/1986 | Cain |
| 4,755,139 A | 7/1988 | Abbatte et al. |
| 4,793,803 A | 12/1988 | Martz |
| 4,798,534 A | 1/1989 | Breads |
| 4,856,991 A | 8/1989 | Breads et al. |
| 4,880,380 A | 11/1989 | Martz |
| 5,013,239 A | 5/1991 | Kesling |
| 5,035,613 A | 7/1991 | Breads et al. |
| 5,055,039 A | 10/1991 | Abbatte et al. |
| 5,059,118 A | 10/1991 | Breads et al. |
| 5,145,364 A | 9/1992 | Martz et al. |
| 5,176,517 A | 1/1993 | Truax |
| 5,186,623 A | 2/1993 | Breads et al. |
| 5,415,542 A | 5/1995 | Kesling |
| 5,645,420 A | 7/1997 | Bergersen |
| 5,683,244 A | 11/1997 | Truax |
| 5,692,894 A | 12/1997 | Schwartz et al. |

(Continued)

*Primary Examiner*—Cris Rodriguez
*Assistant Examiner*—Candice C Stokes
(74) *Attorney, Agent, or Firm*—Paul M. Denk

(57) ABSTRACT

Micro-regional force application improves the control of the orthodontic movement of teeth in all six degrees of freedom. Micro regional force application utilizes an elastic repositioning appliance, a tooth positioner, a polymeric shell, or preprogrammed series of polymeric shells. The key components of the invention are the envelope of freedom, the force applicators, force couplers, counterpart coupling, vector modifiers, seating guides, decouplers, and forced balance points. Further, computerized finite element analysis determines the center of resistance and the center of rotation for each tooth to be moved. The present invention gently rotates and translates one or more teeth to a desired straight position within a treatment plan.

9 Claims, 11 Drawing Sheets

U.S. PATENT DOCUMENTS

| | | |
|---|---|---|
| 5,975,893 A | 11/1999 | Chishti et al. |
| 6,217,325 B1 | 4/2001 | Chishti et al. |
| 6,299,440 B1 | 10/2001 | Phan et al. |
| 6,309,215 B1 | 10/2001 | Phan et al. |
| 6,318,994 B1 | 11/2001 | Chishti et al. |
| 6,371,759 B1 | 4/2002 | Schwartz |
| 6,398,548 B1 | 6/2002 | Muhammad et al. |
| 6,406,292 B1 | 6/2002 | Chishti et al. |
| 6,450,807 B1 | 9/2002 | Chishti et al. |
| 6,454,565 B2 | 9/2002 | Phan et al. |
| 6,471,511 B1 | 10/2002 | Chishti et al. |
| 6,524,101 B1 | 2/2003 | Phan et al. |
| 6,554,611 B2 | 4/2003 | Chishti et al. |
| 6,572,372 B1 | 6/2003 | Phan et al. |
| 6,582,227 B2 | 6/2003 | Phan et al. |
| 6,626,666 B2 | 9/2003 | Chishti et al. |
| 6,629,840 B2 | 10/2003 | Chishti et al. |
| 6,682,346 B2 | 1/2004 | Chishti et al. |
| 6,685,469 B2 | 2/2004 | Chishti et al. |
| 6,699,037 B2 | 3/2004 | Chishti et al. |
| 6,702,575 B2 | 3/2004 | Hilliard |
| 6,705,863 B2 | 3/2004 | Phan et al. |
| 6,722,880 B2 | 4/2004 | Chishti et al. |
| 6,767,208 B2 | 7/2004 | Kaza |
| 6,783,360 B2 | 8/2004 | Chishti |
| 6,786,721 B2 | 9/2004 | Chishti et al. |
| 6,802,713 B1 | 10/2004 | Chishti et al. |
| 6,830,450 B2 | 12/2004 | Knopp et al. |
| 6,948,931 B2 | 9/2005 | Chishti et al. |
| 6,964,564 B2 | 11/2005 | Phan et al. |
| 2005/0106525 A1* | 5/2005 | Knopp et al. .................. 433/6 |

\* cited by examiner

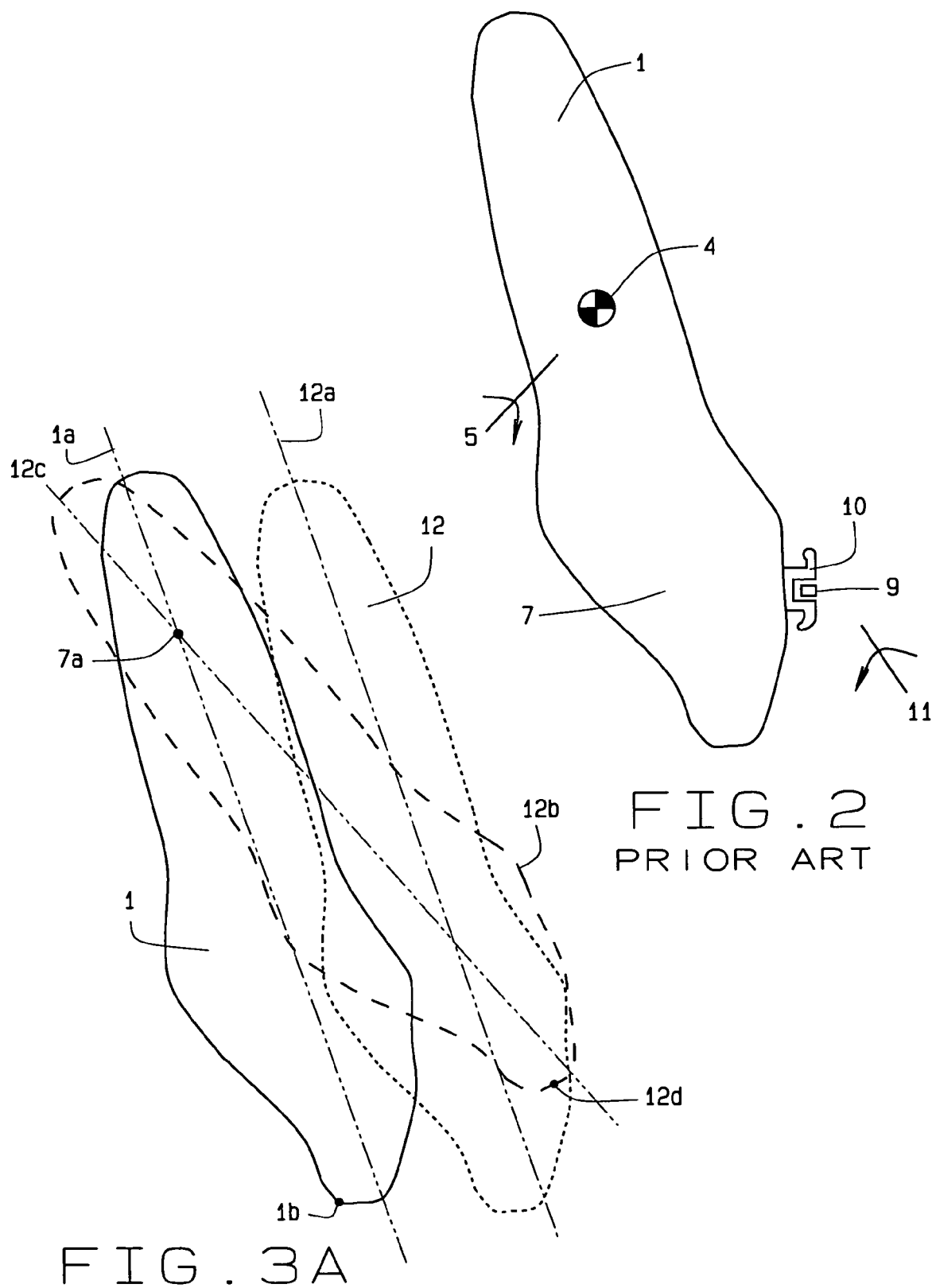

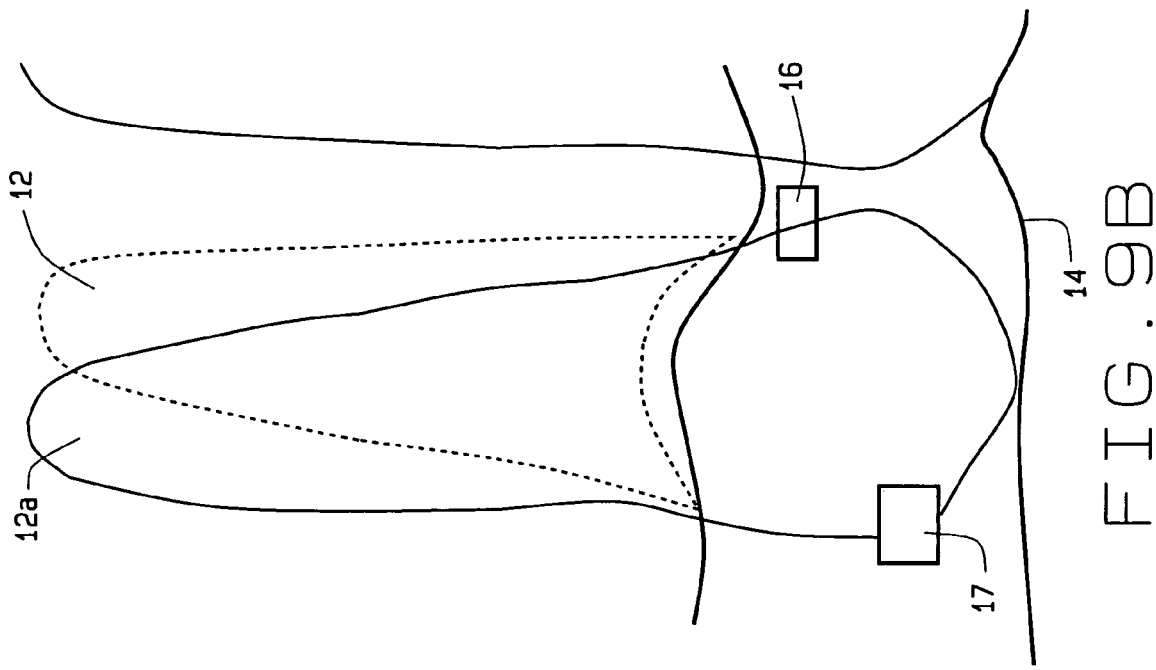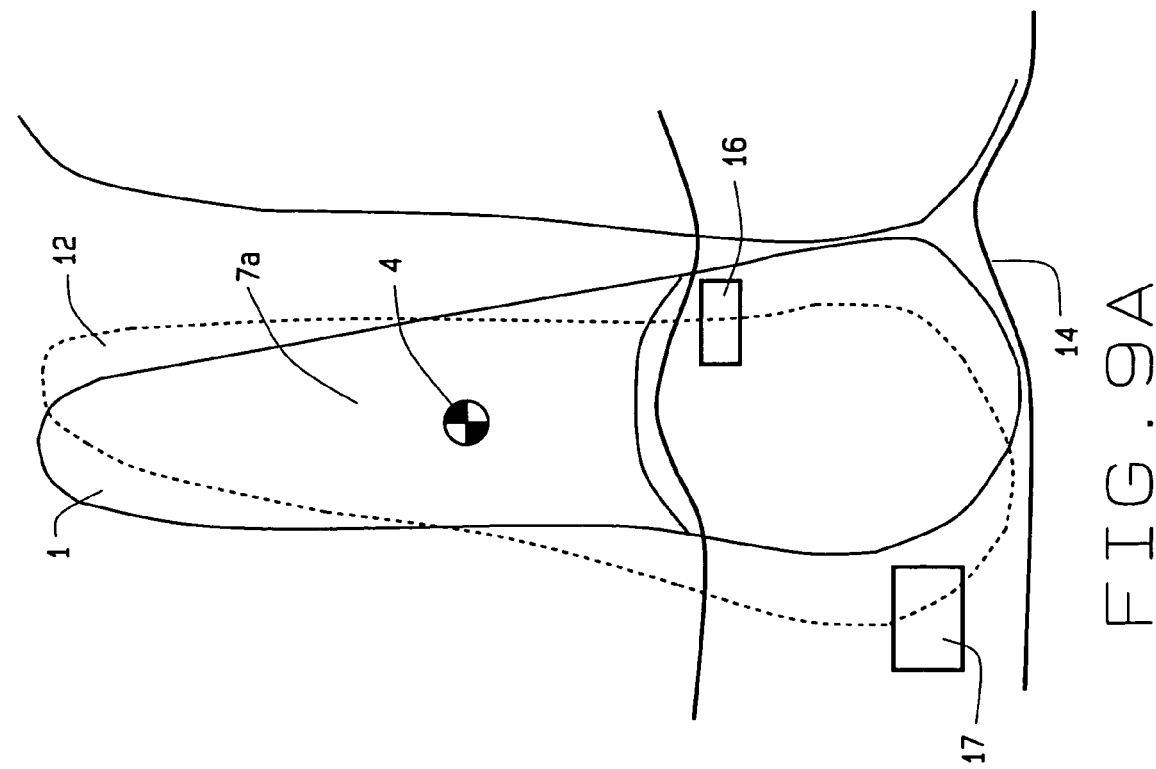

SYSTEM AND METHOD FOR IMPROVED CONTROL OF TOOTH MOVEMENT WITH ELASTIC REPOSITIONING APPLIANCES

CROSS REFERENCE TO RELATED APPLICATION

This non-provisional application claims priority to the provisional application for patent Ser. No. 60/666,908 which was filed on Mar. 31, 2005.

BACKGROUND OF THE INVENTION

This invention relates to realignment of teeth, and more specifically pertains to the micro-regional force applications that tighten the control of the orthodontic movement of teeth in multiple directions.

The field of dentistry known as orthodontics involves applying forces to teeth in their current positions to create stresses in the periodontal ligament which connects the teeth to the supporting bone. These stresses stimulate the apposition and resorption of the supporting bone matrix allowing the teeth to be repositioned in the matrix to the position desired by the treating dentist. The direction, magnitude, range and relative positions on a tooth of the forces applied, in combination with the properties of an individual tooth to be moved, determine the actual versus desired movement of the tooth.

Currently orthodontic forces are applied to teeth with a variety of force generators including wires, brackets and bands bonded to the teeth, springs, elastomerics, and elastic repositioning appliances or tooth positioners sometimes in the form of a polymeric shell or a series of polymeric shells. With conventional braces, a force is generated when a flexible arch wire is distorted and secured into a slot in a bracket bonded to a tooth. As the wire seeks its original shape, a force is created. Because the force is applied a distance from the center of resistance, $C_{Res}$, of a tooth, a moment is created that induces the tooth to rotate. To control the rotation, the wire would be rectangular or square in cross-section and the rectangular slot in the bracket fits tightly around the wire. A controlling couple arises as the flat portions of the wire engage the flat portions of the bracket. The sum of the moment of the couple and the moment of the force determined if and how the tooth will rotate with positive and negative being assigned to the directions of rotation. The analysis of these forces centers upon the $C_{Res}$. The forces generated by prior art elastic repositioning appliances, polymeric shells or tooth positioners are less controlled due to the difficulty in creating precise couples as a result of the imprecise location, magnitude and direction of the forces they generate.

Orthodontic tooth movement forces generated by elastic repositioning appliances, polymeric shells or tooth positioners as applied in the prior art are described in U.S. Pat. Nos. 6,786,721; 6,783,360; 6,767,208; 6,722,880; 6,699,037; 6,685,469; 6,682,346; 6,629,840; 6,626,666; 6,582,227; 6,572,372; 6,554,611; 6,471,511; 6,454,565; 6,450,807; 6,406,292; 6,398,548; 6,318,994; 6,309,215; 6,299,440; 6,217,325; 5,975,893; 5,186,623; 5,059,118; 5,055,039; 5,035,613; 4,856,991; 4,798,534; 4,755,139. The preceding patents have the problem of controlling the tooth rotations created upon all axes generated by the unwanted moments induced by the imprecise forces applied to the teeth. These rotations and forces create unwanted side effects including deviating from the intended treatment path or plan. With early generations of these elastic repositioning appliances, movement was limited to one or two simple stages and the error introduced by rotation was of little importance to achieving the desired outcome.

Then U.S. Pat. Nos. 6,786,721; 6,783,360; 6,767,208; 6,722,880; 6,699,037; 6,685,469; 6,682,346; 6,629,840; 6,626,666; 6,582,227; 6,572,372; 6,554,611; 6,471,511; 6,454,565; 6,450,807; 6,406,292; 6,398,548; 6,318,994; 6,309,215; 6,299,440; 6,217,325; 5,975,893, all pertain to a system and method where the initial tooth position creates an initial digital data representation of the dentition, a final target tooth arrangement is created as a final digital representation, and intermediate transitional tooth arrangements are described digitally to plan an orthodontic treatment. The orthodontic treatment is established at the beginning of treatment and has many transitional tooth arrangements over an extended time period. A polymeric shell appliance is created to correspond to each transitional arrangement. Each appliance has a cavity to receive at least one tooth whose geometry corresponds to the next transitional tooth arrangement. The prior art has shortcomings explained below that the present invention overcomes.

In the prior art, the orthodontic force arises haphazardly by the poor fit of prior art appliances to the current arrangement of the teeth and with the location, magnitude, range and direction of the forces determined by the geometry of the next transitional stage regardless of the effectiveness of those forces. The present invention sets up effective forces and moments but not ideal or perfect forces and moments. Computer modeling of teeth, used to determine the final tooth arrangement from an orthodontic treatment path, excludes supporting structures such as root length, root shape, bone height, root surface area, and the position of forces applied to these structures.

When the appliance is installed, the poor fit of the appliance distorts its shape, which creates an orthodontic force as it tries to return to its shape. As the appliance approaches its undistorted geometry, the force dwindles because the magnitude of the force is a function of the degree of distortion. This decrease in orthodontic force can limit the intended movement, as the force drops below an effective therapeutic level before reaching the target transitional tooth position. This shortfall, as a result of inadequate force, though of little significance in a short sequence of appliances, may accumulate in a longer series of appliances thus deviating from the intended treatment path.

Controlling the rotational moment of the orthodontic force inherent in prior art flexible-positioning appliances that cause tooth rotation away from the intended treatment becomes more difficult by the cumulative effect of successive appliances, e.g. if each appliance creates a 2° unintended rotation, then over ten appliances the effect grows to 20°. A minor problem with one or two appliances now introduces a major error when applied over a greater number of appliances.

Referring to FIG. 3A, from the initial data of the tooth position, treatment is planned to advance the tooth bodily, with no rotation, to the final position. The long axis of the initial, and final tooth positions are preprogrammed to be parallel. If the tooth during treatment experiences unintended tipping, the long axis of the tooth will be inclined relative to the preprogrammed position. Because the existing polymeric shells were manufactured to fit a tooth with no rotation, and the tooth occupies a rotated position, a gap arises between the incisal edge of the tooth, and the polymeric shell creating the false appearance of intrusion. FIG. 3B shows where the teeth 1 have rotated around a different axis of rotation than planned in the appliances 2 creating the false appearance of intrusion with gaps 3 between the incisal edges of the teeth 1 and the appliances 2. This commonly occurs with a series of polymeric appliances, especially in the prior art. Accurate computer modeling of tooth movement from applied forces attempts to reduce false intrusion. However, common computer modeling in the absence of increased control of forces permits unwanted deviation from a narrow treatment path.

To prevent unwanted rotations and apparent intrusion the prior art has tightened the grip between the appliance and the tooth by adding protrusive attachments as later shown in FIG. 4 and varying the elastic modulus of the appliance; see U.S. Pat. Nos. 6,830,450; 6,705,863; 6,572,372; 6,524,101; 6,454,565; 6,309,215; and 5,176,517. This approach has seen marginal success because as a tooth rotates around a different axis of rotation than that of the polymeric appliance program, the grip of the attachment quickly loosens as it pulls out of the receptacle when the gingival portion of the tooth falls behind the rotating appliance. Once the attachment loosens unintended, unfavorable forces may arise and the options to recapture the tooth dwindle.

Controlling unwanted rotation with attachments also faces unfavorable physics. Referring to FIG. 5A, if the polymeric appliance apples 100 g of force on the attachment to move a tooth at 10 mm from the $C_{Res}$, a moment of 1000 g*mm arises. To prevent tipping of a tooth, a couple must have equal magnitude and opposite direction to the moment. If the attachment is 4 mm long, and that all force applies at the ends, then an equal and opposite couple force is 1000 g*mm/4 mm or 250 g. This force exceeds that which the appliance can resist, the appliance displaces, and unwanted rotation occurs.

Rotation of a tooth around the vertical axis defies prediction in the prior art because the attachments commonly pull out of the polymeric shell. Effectively, the polymeric shell cannot distort in a mesial or distal direction. When using elastic repositioning appliances or tooth positioners in the form of polymeric shells, the predictable forces generated by the distortion of the appliance act buccally and lingually. FIG. 5B illustrates a poorly fit polymeric shell when placed over a tooth to be rotated, because the appliance cannot distort efficiently in a mesial or distal direction, the attachment will not fit into its concavity. The majority of force generated by the poorly fit appliance causes no orthodontic movement in the intended direction. The force generated in a therapeutic direction has no couple force to produce effective rotation and so the tooth falls behind the treatment plan.

In consequence, the above described deviations from the intended treatment path may cause the remaining appliances to have marginal effect or become unusable. Modifications to the prior art appliances is extremely limited. Reconfiguration of the appliance sequence to remedy the new, though unintended, tooth position calls for new impressions of the patient's teeth and expensive and lengthy rework of the appliance sequence.

SUMMARY OF THE INVENTION

This invention uses and applies elastic repositioning appliances, upon select teeth, improves control over tooth movement, and provides for better tooth alignment and straightening, as determined by the treating dentist as necessary to correct natural tooth placement. Essentially, the invention utilizes elastic positioning means, or tooth positioners, sometimes as a series of preprogrammed polymeric shells, and which provide for the orthodontic movement of teeth in all six degrees of freedom shown in FIG. 6c, to align teeth correct various orthodontic problems. Perimetrical force placement, micro-regional force, and counterpart coupling, in the form of force applicators, force couplers, vector modifiers, and decouplers with the moving tooth surrounded by an envelope of freedom, precisely direct the orthodontic force generated by elastic repositioning or tooth positioner appliances. Computer aided finite element analysis, for predicting tooth movement, markedly enhances the quality of treatment outcome. With these means, the vectors of force that move a tooth in a plurality of directions, that achieve alignment, of that tooth, with adjacent teeth, can be determined. Through the usage of the repositioning appliances, this invention, repositions teeth into their proper determined locations as planned.

The concept of this invention recognizes that:

1) Elastic repositioning appliances rely upon a force transverse across a tooth, facial to lingual or lingual to facial;

2) Single forces applied to the crown of a tooth induce a rotational moment that must be controlled;

3) Combinations of forces are required to control movement in all six degrees of freedom;

4) Accurate modeling of the actual against the predicted tooth movement is vital to the success of treatment, where personalized variables when included in the tooth movement model more closely duplicate clinical outcomes;

5) To control the tooth movement effectively with repositioning appliances, the force application location, direction, magnitude and range must be tightly controlled;

6) Opposing forces of equal magnitude applied at different distances from the $C_{Res}$ cancel the translational force but create a rotational moment;

7) The amount of force generated by the force applicator, force coupler, or decoupler is a function of the amount of appliance deflection and the location on the appliance, and can be calculated or estimated. More force is generated per 0.1 mm of deflection as one moves occlusally in the appliance;

8) To keep the force applicators functional through the entire planned movement for each stage, extra deflection must be built in, particularly as the appliance or shell approaches the target or final position and to keep the force applicators functional throughout the planned movement for each treatment. An envelope of freedom is required around every tooth to be moved so that contact between the appliance and the tooth is at the planned locations and the envelope of freedom also includes a clear path of movement to ease projected tooth movement;

9) Vector modifiers are not attachments as described in U.S. Pat. Nos. 6,830,450; 6,705,863; 6,572,372; 6,524,101; 6,454,565; 6,309,215; and 5,176,517 since they are not enclosed or captured by the appliance. The intent is not to hold a tooth but to modify the vector of force created by the one surface contact with the force applicator;

10) The geometry of the elastic repositioning appliance around teeth not being moved should contact as much surface area as possible to maximize the retention of the appliance and provide anchorage. Protrusions may be added to the anchor teeth to enhance retention of the appliance as described in U.S. Pat. Nos. 6,830,450; 6,705,863; 6,572, 372; 6,524,101; 6,454,565; 6,309,215; and 5,176,517; and, 11) Teeth can be moved and rotated in a stepwise fashion that reverses the rotational direction and moves the axis of rotation to achieve effective bodily translation; and, 12) Treatment can be divided into stages with each having an individual appliance or shell and thus the sum of all of the stages defines the complete treatment from the starting to the final configuration of a tooth or teeth.

The nature of the elastic repositioning appliance creates an opportunity to apply forces from directions and in combinations previously unavailable. In general, with this invention, the most effective forces to control rotations and tooth movement arise from force placement directed to the perimeter of the tooth as viewed from the facial or lingual and are applied at multiple points on the tooth either concurrently or sequentially.

This invention of micro-regional force application greatly improves the control of the orthodontic movement of one or more teeth in all six degrees of freedom using elastic repositioning appliances or tooth positioners sometimes in the form of polymeric shells or a preprogrammed series of polymeric shells. The key components of this invention are:

the envelope of freedom, force applicators, force couplers, vector modifiers, seating guides, decouplers, force balance points, micro-regional force application and perimetrical force placement.

This invention also incorporates computer aided finite element analysis that determines a center of resistance and center of rotation for each tooth to be moved in the calculations of the predicted path of movement. The center of resistance and the center of rotation are determined from variables including but not limited to root length, roto surface area, root shape, force position, and bone height. The combination of the application of micro-regional forces and an improved movement model greatly increased the clinical control available to the treating doctor. The quality of the orthodontic treatment directly relates to the degree of control available to the doctor during treatment. By improving the control available with elastic repositioning appliances and tooth positioners, such as polymeric shells or a preprogrammed series of shells the treatment quality vastly improves.

It is, therefore, the principal object of this invention to provide elastic repositioning means, in the form of an appliance, that allows for shifting of teeth which can be rotated or moved in a stepwise fashion by forces exerted from a variety of directions, to align teeth better.

These and other objects may become more apparent to those skilled in the art upon review of the summary of the invention as provided herein, and upon undertaking a study of the description of its preferred embodiment, in view of the drawings.

BRIEF DESCRIPTION OF THE DRAWINGS

In referring to the drawings,

FIG. 2 shows the type of forces generated utilizing a prior art brace, applying a flexible arch wire in location;

FIG. 3A shows tooth treatment provided to advance a tooth bodily, with no rotation to the final digital representation position as represented by the final aligned tooth (shown in phantom);

FIGS. 9A and 9B show how the tooth is translated with angulation rotation control by the force applicators and force couplers;

DESCRIPTION OF THE PREFERRED EMBODIMENT

Figure 1A:
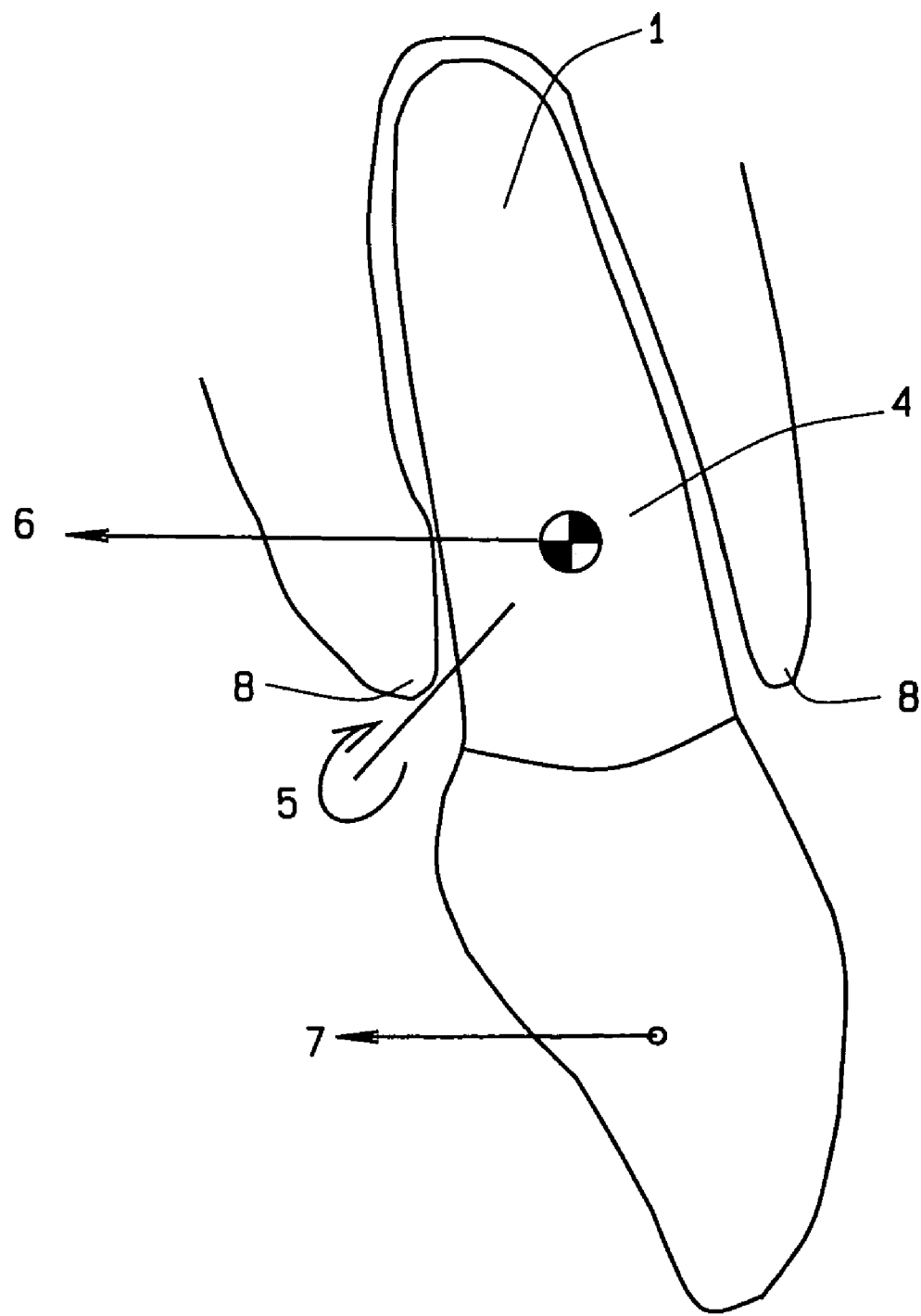
FIG. 1A shows the forces applied to a tooth generally around a point identified as the "center of resistance" or $C_{res}$.
Figure 1B:
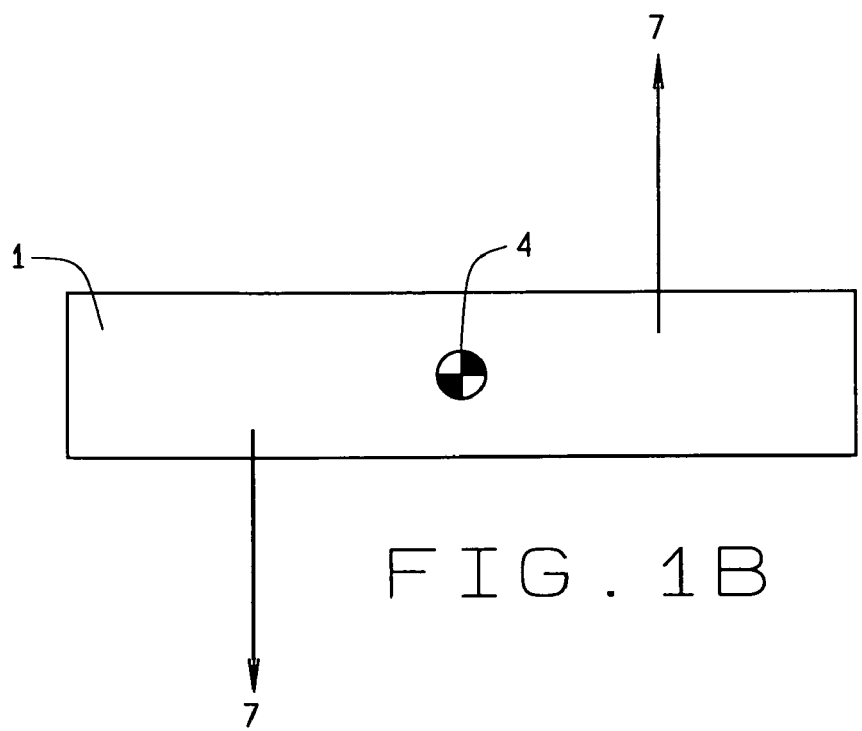
FIGS. 1B and 1C disclose the application of opposing parallel forces of equal magnitude for producing rotational forces upon the treated tooth.
Figure 1C:
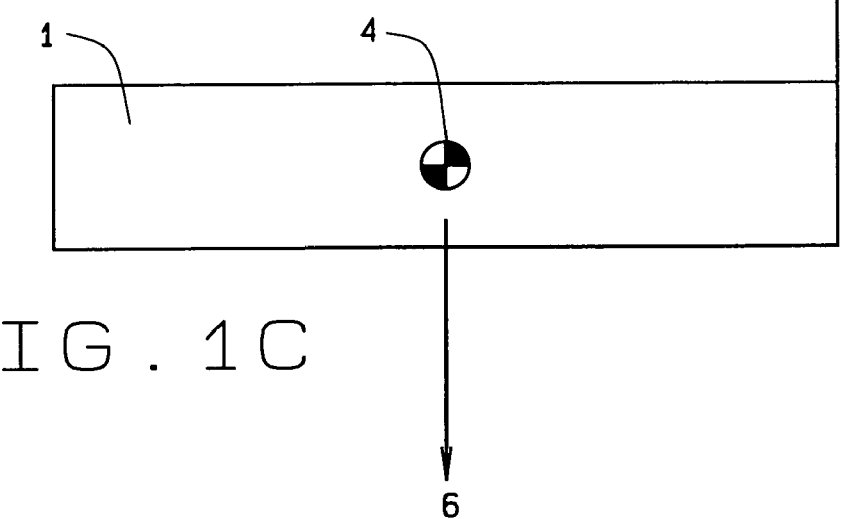
Figure 1D:
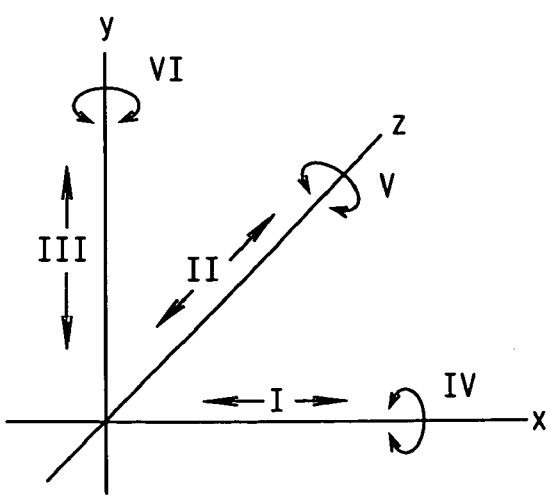
FIG. 1D shows the six degrees of freedom a tooth can be moved in three dimensional space.

This invention improves the control of the orthodontic movement of teeth in all six degrees of freedom of movement. FIG. 1D shows the six degrees of freedom for movement of a treated tooth by utilizing the plastic repositioning appliance or the tooth positioner. Translation is shown by the x, y, z axes enumerated at i, ii, iii respectively and moment is shown by rotation about the x, y, z axes enumerated as iv, v, vi respectively. The tooth positioner of the present invention is a polymeric shell, individually, or in series.

The prior art devices provide for shifting and movement of teeth, but with limited control and unintended movement. For example in FIG. 1, the forces applied to a tooth 1 are evaluated around a point called the "center of resistance" $C_{Res}$ 4 which is the orthodontic equivalent of the center of mass. A single force applied at any location other than the $C_{Res}$ creates a rotational effect measured as a moment 5. All forces and moments applied to a tooth are measured relative to $C_{Res}$. When a force 6 is applied to a tooth through the $C_{Res}$ no moment arises therefore the tooth does not rotate and it is translated bodily. When a force 7 is applied at a distance from the $C_{Res}$, a rotational moment 5 is created equal to the force multiplied by the distance. Generally, a single orthodontic force produces a force and a moment that induces some combination of translation and rotation because forces are applied above the gingival line and the $C_{Res}$ is always below the crest of supporting bone 8. Controlling that rotation is a key element of controlling orthodontic force and producing the desired movement. Referring to FIG. 1B a couple is two parallel forces 7 of equal magnitude applied to an object such as a tooth 1 with lines of action in opposite directions. The translational effects of the forces cancel out; however, the forces combine to produce a moment around the $C_{Res}$ equal to the magnitude of one force multiplied by the distance between them regardless of the location on the tooth. For example, in FIG. 1B, if the forces 1 are 100 g and the distance between them is 10 mm, then the moment would be 100 g×10 mm=1000 g*mm. Looking at FIG. 1C, we can calculate each moment individually:

Force 6 is 10 mm from the center of mass; therefore, 100 g×10 mm=1000 g*mm.

Force 2 is 0 mm from the center of mass; therefore, 100 g×0 mm=0 g*mm.

The rotations are the same because the distance between them is the same even though their application points have been moved.

With prior art braces shown in FIG. 2, a force is generated when a flexible arch wire 9 is distorted and ligated into a slot in a bracket 10 bonded to a tooth 1. As the wire seeks its original shape, a force 7 arises. Because the force 7 is applied a distance from the $C_{Res}$ 4, a moment 5 is created that induces the tooth 1 to rotate and translate. To control the rotational tendency, the wire used is rectangular or square in cross section and the rectangular slot in the bracket 10 fits tightly around the wire 9. A controlling couple 11 is created as the flat portions of the wire 9 engage the flat portions of the bracket 10. The sum of the moment of the couple 11 and the moment 5 of the force determine if and how a tooth rotates. The analysis of these forces is based upon the $C_{Res}$, however the couple 11 is shown around the bracket 10 for clarity. The forces generated by elastic repositioning appliances, polymeric shells or tooth positioners are less controlled due to the difficulty of creating couples and the imprecise locating and directing of the forces.

Figure 3B:
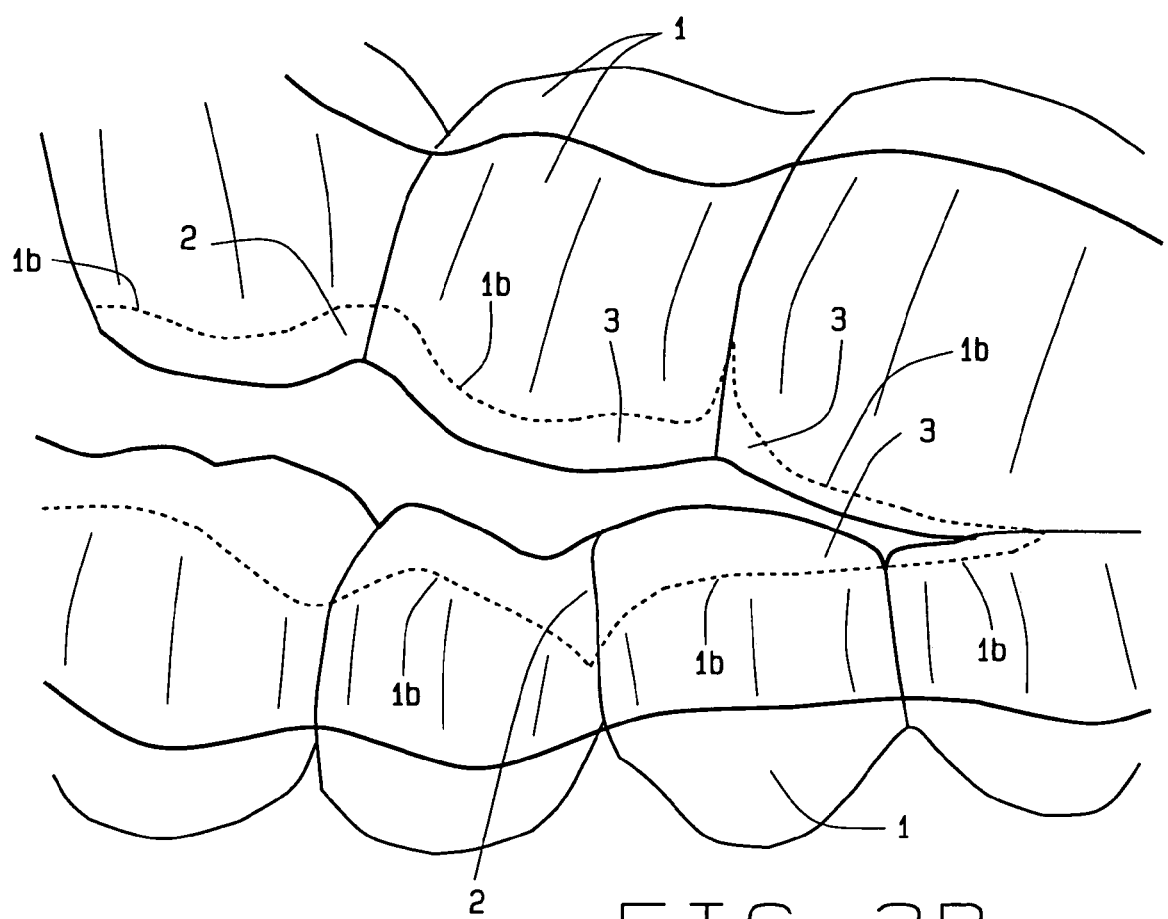
FIG. 3B is a photo showing the actual application of a repositioning appliance.

Referring to FIG. 3A, based upon the initial data, a tooth treatment plans to advance a tooth bodily using a preprogrammed series of prior art polymeric shells, with no rotation to the final position represented by tooth 1. The long axes 1a, 12a of tooth 1, 12 respectively will be parallel. Because a polymeric shell was manufactured to fit tooth in position 12, but the tooth is in actually another position, a gap 3 appears between the incisal edge of the tooth and the polymeric shell at a distance creating an apparent intrusion. FIG. 3B is a photo of a clinical example where the teeth 1 have rotated around a different axis of rotation than planned in the appliances 2 creating the apparent intrusion with a gap 3 between the incisal edge of the teeth 1 and the appliances 2. This apparent intrusion occurs often with a series of polymeric appliances. Apparent intrusion present a twofold issue: first, the appliance or shell did not control the inclination of the tooth thus producing undesirable tooth movement, and second, the digital model failed to predict accurately the effect of the orthodontic appliance.

Figure 4:
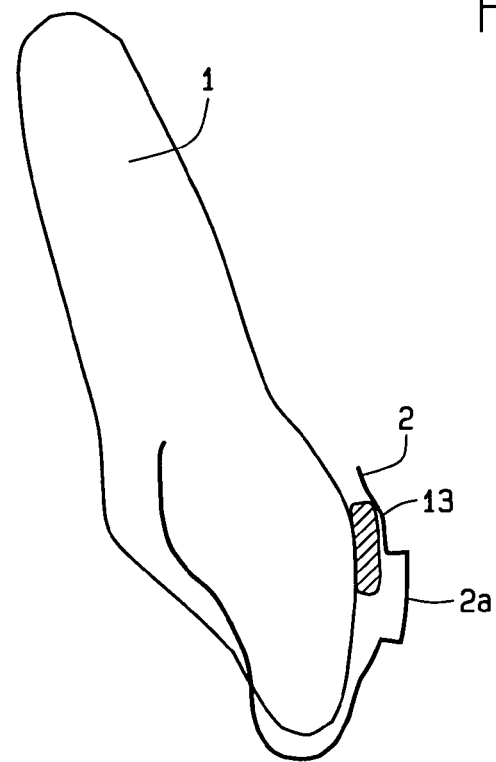
FIG. 4 discloses the prior art method that tightens the grip between the appliance and the tooth.

To prevent unwanted rotations and apparent "intrusion" the prior art has tightened the grip between the polymeric appliance and a tooth 1 shown in FIG. 4, by adding protrusive attachments 13 and varying the elastic modulus of the appliance. The prior art has had only marginal success because as the tooth 1 rotates around a different axis of rotation than the program of the polymeric appliance 2, the grip on the attachment 13 is quickly lost as it pulls out of the attachment receptacle 2a when the gingival portion of the tooth falls behind the appliance due to rotation. The marginal success comes from the appliance's inability to produce an effective couple and the computer model's lack of key individualized variables. Upon loss of the engagement of the attachment, unfavorable forces limit recapture of the tooth in a programmed treatment.

Figure 5A:
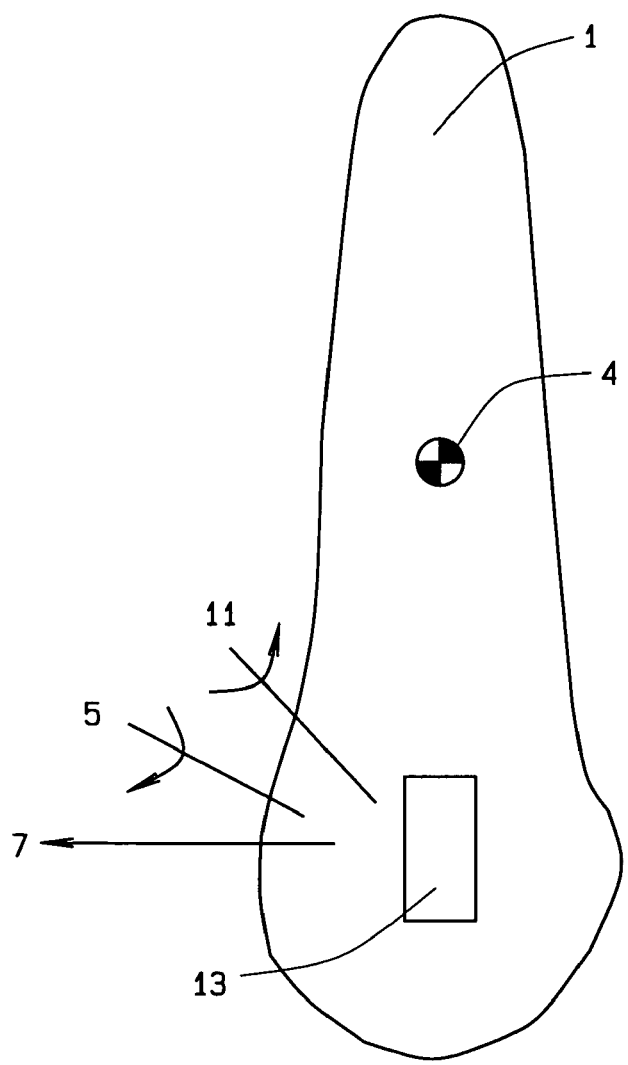
FIG. 5A shows a prior art polymeric appliance method that applies directional forces onto the tooth to move it.

Another problem with controlling unwanted rotation with prior art attachments comes from the unfavorable physics. Referring to FIG. 5A, where a polymeric appliance applies 100 g of force 7 on the attachment 13 to move the tooth, and the force is 10 mm from the $C_{Res}$ 4 1000 g*mm of moment 6 arises. To prevent tipping, the tooth requires a couple of equal magnitude and opposite direction. If the attachment 13 is 4 mm long, and all of the force is applied at the ends, then an equal and opposite couple 11 requires 1000 g*mm/4 mm or 250 g of force. This force exceeds the resistance of the appliance, the appliance displaces, and unwanted rotation occurs. As before, upon loss of the engagement of the attachment, unfavorable forces limit recapture of the tooth in a programmed treatment.

Figure 5B:
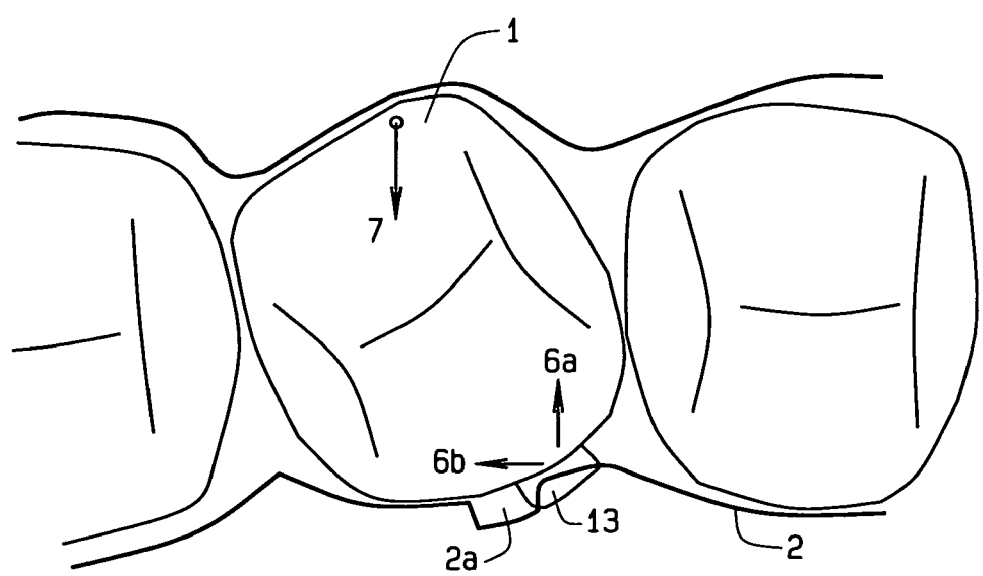
FIG. 5B discloses use of elastic repositioning appliance method heretofore utilized to effect rotation around the vertical axis.

Rotation of a tooth around the vertical axis defies prediction because the attachment commonly pulls out of the polymeric appliance. Here, the polymeric appliance cannot distort efficiently in a mesial or distal direction. When using elastic repositioning appliances, tooth positioners, or polymeric shells, all significant forces generated by the distortion of the appliance are buccal and lingual. FIG. 5B illustrates when a poorly fit polymeric appliance 2 is placed over the tooth 1 to be rotated clockwise, because the polymeric appliance can not distort efficiently in a mesial or distal direction, the attachment 13 does not fit well into the concavity or receptacle 2a provided for it. The majority of force 6a is offset by force 7 causing no orthodontic movement. The minor force generated in a distal direction 6b has no coupling force to produce effective rotation and so the tooth falls behind the programmed rotation.

Figure 6C:
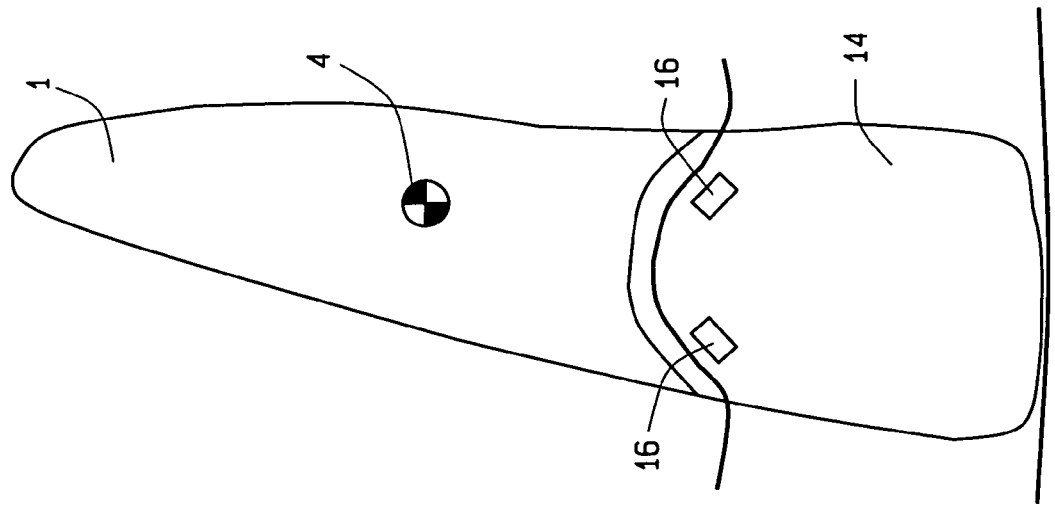
FIGS. 6A, 6B, 6C show side, facial and lingual views respectively of the present invention, a polymeric shell, applied to a tooth to attain an envelope of freedom, force applicators, and force couplers.
Figure 6B:
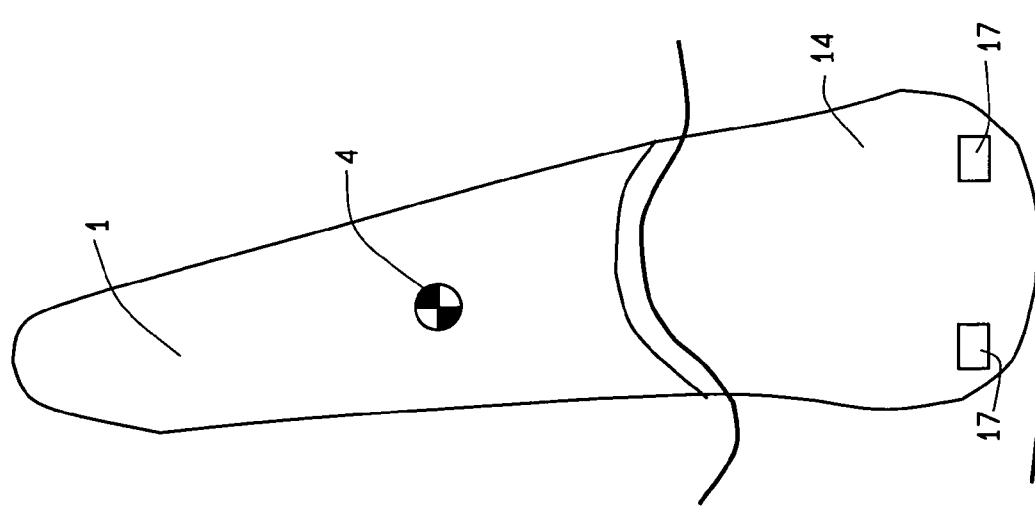
Figure 6A:
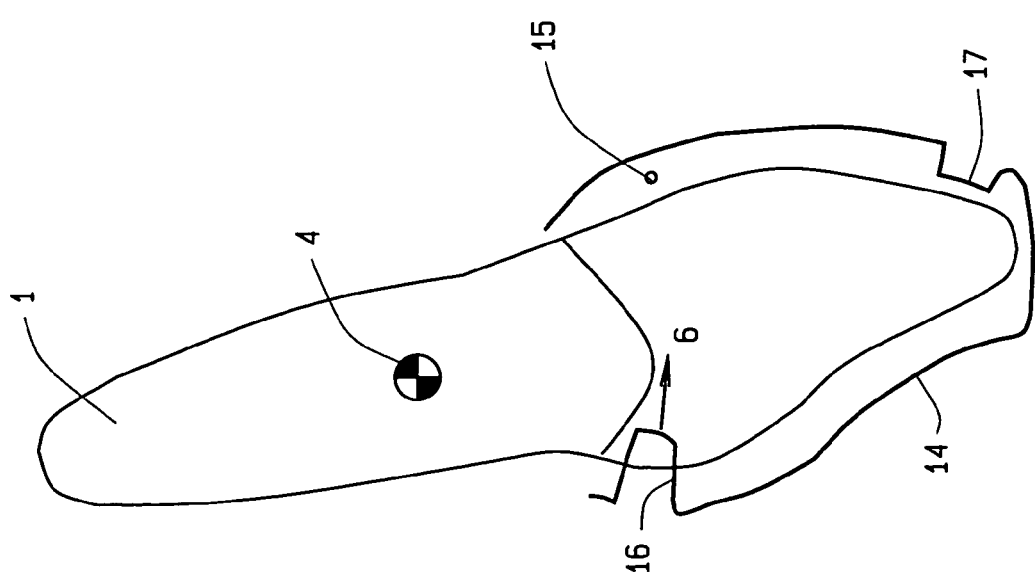

Referring to FIG. 6A, side view of a shell upon a tooth, FIG. 6B facial view of a shell upon a tooth, and FIG. 6C, lingual view of a shell upon a tooth, the present invention of a polymeric shell 14 includes an envelope of freedom 15 with clearance between the tooth 1 and the present invention in most directions, except occlusally, from the starting position through to the desired target position. An envelope of freedom, around every tooth to be moved, ensures that contact between the appliance and the tooth occurs only in the planned locations. To control the magnitude, direction and location of the forces precisely as applied by the polymeric shell or appliance, projections, in or on the appliance or shell, or force applicators 16 and force couplers 17, are built into the appliance to create micro-regional force applications, with a specific level of force, range, and direction, in exact locations determined by the desired movement. This invention departs from the orthodontic bracket/force in the center of the tooth mindset of the prior art and finely tunes application of force and applies forces to any exposed surface of the tooth to translate the tooth and control rotations with an elastic repositioning appliance.

The projections that provide the driving force 6 to start the translation and rotational processes are called force applicators 16. The projections that are secondarily contacted to receive the tooth after the initial movement are called force couplers 17. The combination of forces produced by these elements, called counterpart coupling, produce the moments needed for control during orthodontic treatment. These projections 16, 17 are usually placed on each tooth 1 in at least two locations with four locations being most common. To gain maximum control of the moments generated by the forces, the distance between the force applicators 16 and force couplers 17 is maximized. To induce rotations, the distance to the $C_{Res}$ of the axis of rotation is also maximized. To reduce unwanted rotations, the distance between the projections 16 and the $C_{Res}$ 4 or axis or rotation should be minimized. In general, to maximize their effect, force applicators and couplers are distributed around the perimeter of the tooth from a facial and lingual view thus separating the force applications for maximum stability and control over the tooth to be moved, also known as perimetrical force placement. Due to the nature of the appliance, the predictable forces generated with elastic repositioning appliances are transverse across the teeth, facial to lingual, or lingual to facial as it is the only predictable distortion of the appliance geometry. Occasionally, vector modifiers, later shown in FIGS. 10A, 10B, 10C attached to the tooth or teeth to be moved can assist in maximizing the available therapeutic force. To clarify the description of the invention, the following sections describe specific movements, but this invention does more than these examples.

Figure 7A:
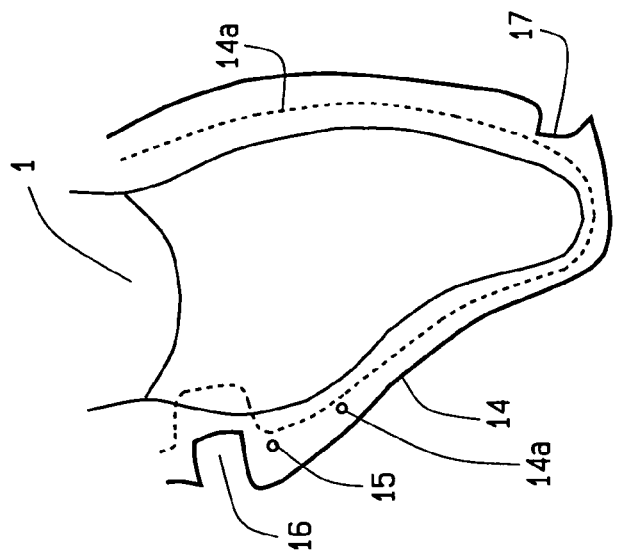
FIGS. 7A, 7B, 7C disclose side, side, and segmental views respectively of a tooth being treated by the present invention to attain labial tooth movement with control of the inclination rotation.

And so, FIG. 7A, describes labial tooth movement with control of inclination rotation. Initially the tooth is surrounded by a polymeric appliance 14 that encloses the tooth and a gap exists, called an envelope of freedom that allows contact between the appliance and the tooth only at the force applicators 16 and force couplers 17 through the planned transition for that appliance. Upon initial placement of the appliance, the force applicators 16 apply a micro-regional force 7 and the tooth 1 rotates around the axis of rotation 7a. The axis of rotation can be estimated as the distance from the $C_{Res}$ 4 using the formula:

$$y=(0.068)(h)^2/d$$

y=the distance between the $C_{Res}$ and the axis of rotation 7a h=the length of the tooth root 1a from the crest of bone 8a, and d=the distance from the force applicator 16 to the $C_{Res}$ 4, Christiansen R L, Burstone C J: Centers of rotation within the periodontal space. Am J. Orthod, 1969; 55(4): 353-369.

This formula simplifies planning as other factors, such as root shape, come into play. To maximize the therapeutic effectiveness of the invention, the integration of the modeling of the axis of rotation into the planned tooth movement includes as many individualized variables as possible. The rotation continues until the tooth 1 makes contact with the force couplers 4 at the rotated.

Figure 7B:
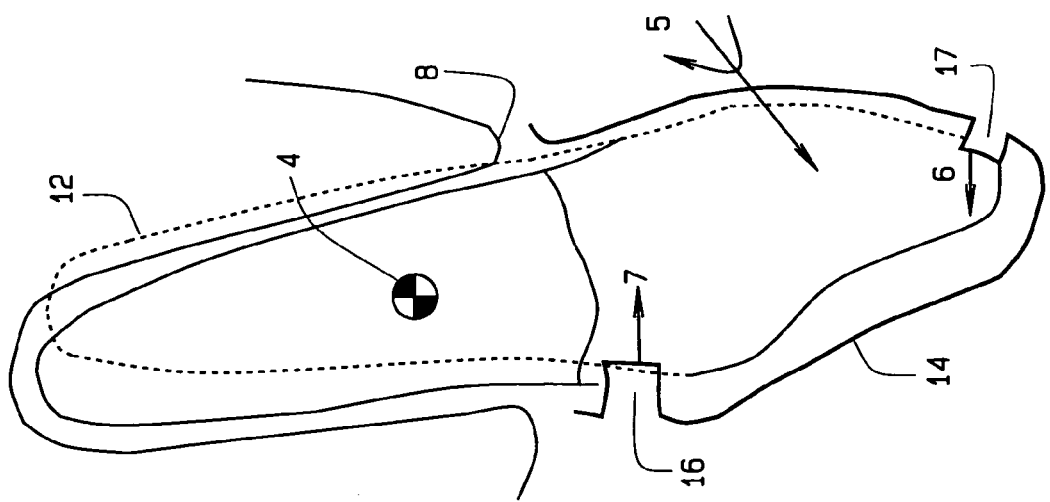
Figure 8C:
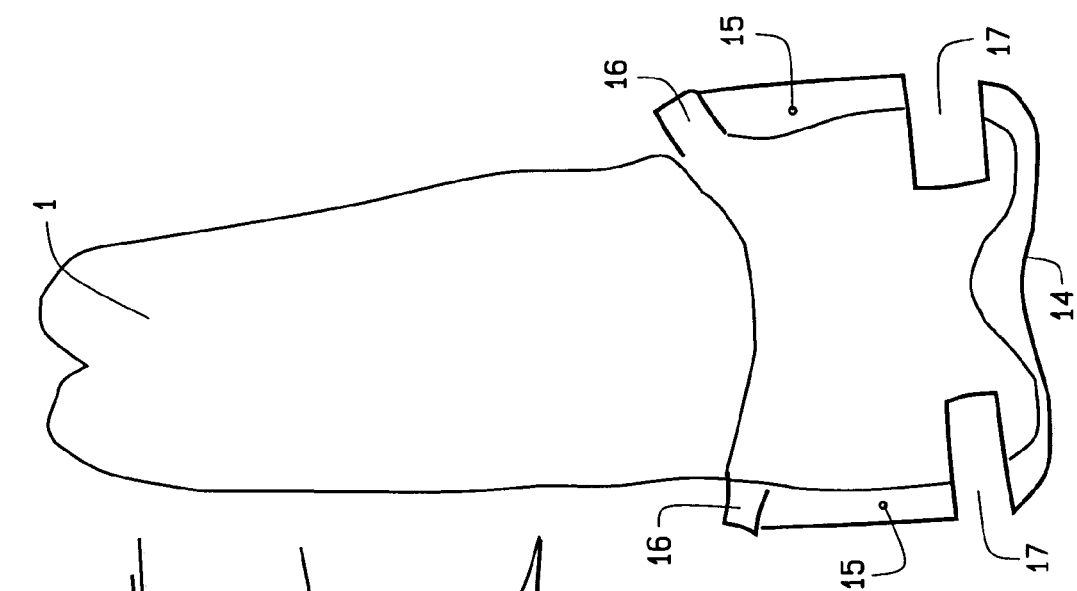
FIGS. 8A, 8B, 8C disclose the facial, occlusal and distal views showing how bodily distal movement of the bicuspid with angulation rotation control, or tip control is achieved.
Figure 8B:
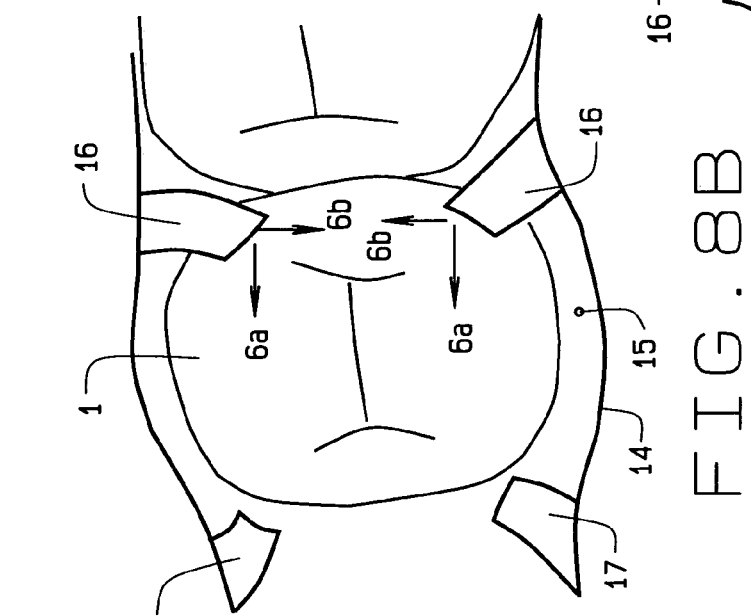

Referring to FIG. 7B, upon contact of a tooth with the force couple 17, an equal and opposite reciprocal micro-regional force 6 arises at the force coupler 17. As the force applicator 16 applies force, the force coupler 17 acts as a fulcrum generating a rotation, called counterpart coupling, with an axis of rotation at 4 that uplifts the root and correcting the previous rotation thus effecting a translational tooth movement with controlled rotation to the second tooth position 12. FIG. 8B also illustrates how the force applicator 16 protrudes slightly beyond the planned final tooth position to maintain adequate orthodontic force through the entire tooth movement and to reach the planned end point for each stage.

Figure 7C:
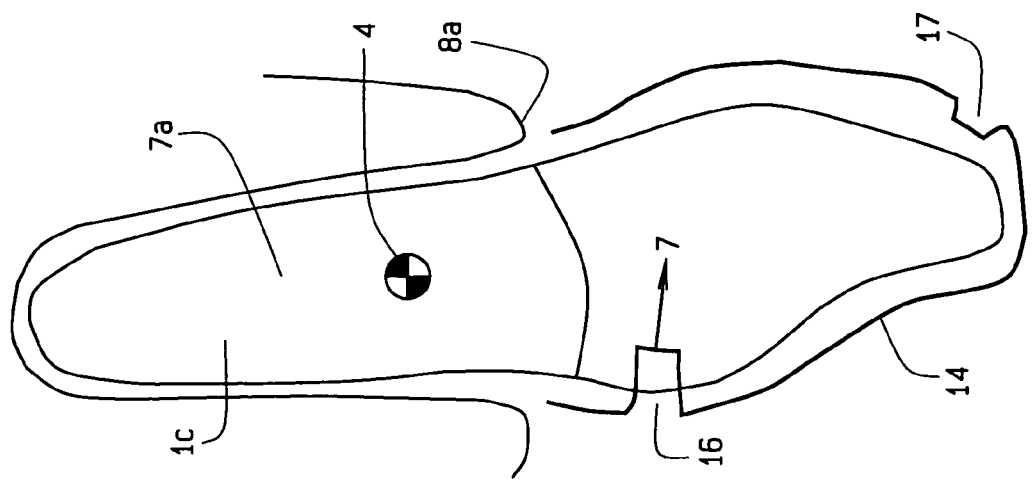

Then FIG. 7C illustrates how when first placed in the mouth, the polymeric appliance 14 will be distorted by the envelope of freedom 15. This distortion creates a force as the resilient appliance 14 seeks its pre-distorted shape.

Figure 8A:
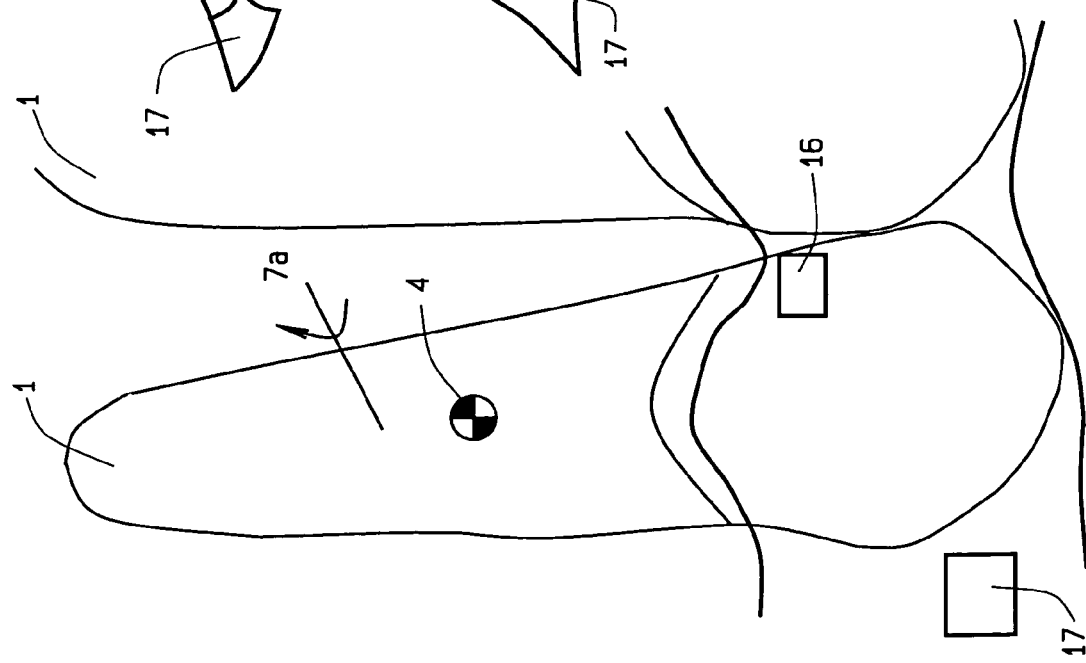

Then FIG. 8A describes the bodily distal movement of a bicuspid with angulation rotation control or tip control. The tooth 1 is surrounded by a polymeric appliance 14 with a gap, called an envelope of freedom 15 that allows contact only between the appliance and the tooth at the force applicators 16 and force couplers 17 through the entire planned transition for that appliance. Upon initial placement of the appliance, the force applicators 16 apply micro-regional forces and the tooth 1 rotates around the axis of rotation 7a.

Next, FIG. 8B illustrates a top or buccal view of the force 6 applied by the force applicators 16 that resolve into vectors 6a and 6b. The buccal and lingual vectors 6b cancel each other, leaving only a distal force 6a. The rotation of FIG. 8A continues until the tooth 1 makes contact with the force couplers 17. FIG. 8C shows a side or distal view of a bicuspid with the present invention in place. The force applicators 16 engage the surface of the tooth in the background and push the tooth towards the force couplers 17 in the foreground. In this view, the force couplers and force applicators are shown symmetrically placed.

Referring to FIG. 9A as the tooth 1 is rotated by the force applicators 16 into the position 12 the force coupler 17 provides an equal and opposite force acting upon a fulcrum. In FIG. 9B, the force coupler generates a rotation, called counterpart coupling, with an axis of rotation at 7a righting the root and correcting the previous rotation thus translating the tooth with controlled rotation to tooth position 12.

Figure 10A:
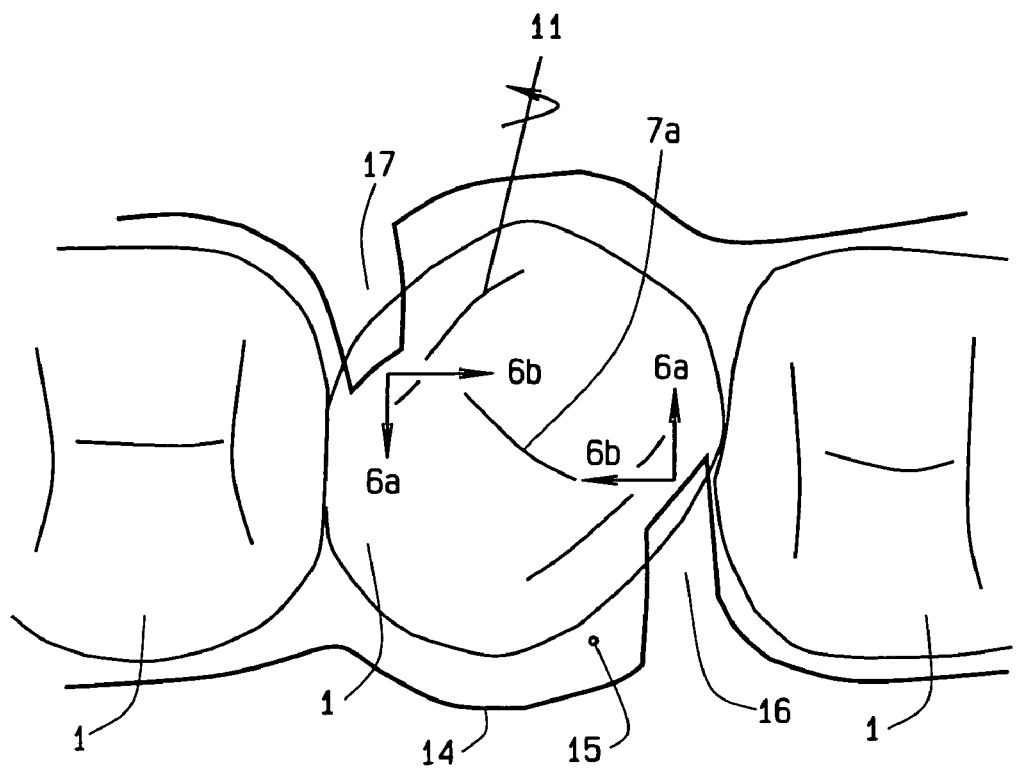
FIGS. 10A and 10B show how the tooth is rotated stepwise around the vertical axis using force applicators with and without vector modifiers.

FIG. 10A describes vertical axis rotation where the tooth 1 is surrounded by a polymeric shell 14 with a gap, called an envelope of freedom 15, that once again only has contact between the appliance and the tooth at the force applicators 16 through the entire planned axial rotation for that appliance. Upon initial placement, the force applicators 16 apply the micro-regional forces 6a and 6b, shown as resolved vectors, and the tooth 1 rotates around the axis of rotation 7a through the vertical length of the tooth. The translational aspects of vectors 6a and 6b cancel each other which leave a net couple 11, also known as counterpart coupling, to rotate the tooth in place. This can be effective, primarily, in an oval tooth form where the mesial/distal dimension exceeds the buccal/lingual dimension because to produce a net couple, the distance of force 6a must be larger than the distance of force 6b.

Figure 10B:
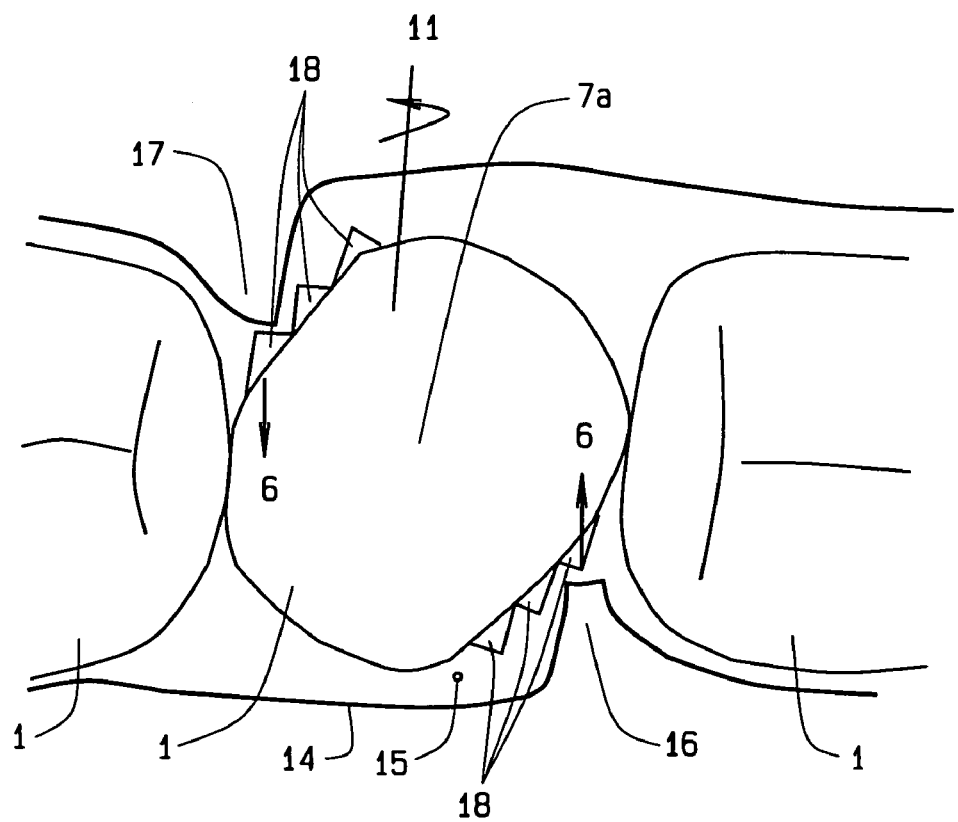

FIG. 10B illustrates rotation of a round tooth with vector modifiers 18. Vector modifiers 18 form in a prefabricated mold with a composite resin bonding procedure or are prefabricated forms directly bonded to the tooth. The vector modifier modifies the force 6 delivered by the force applicator 16 to create a stepped vector for the desired tooth movement, here axial rotation. Multiple vector modifiers 18, initially placed, allow progressive rotation without placing new modifiers. As one shell or appliance completes pushing an individual modifier, that modifier is removed and the next appliance functions against the next modifier. This rotation is not a ratchet or pawl arrangement because of no interlock and a single modifier is used. These are not attachments upon a tooth because they are not captured or enclosed by the appliance or shell.

Figure 10C:
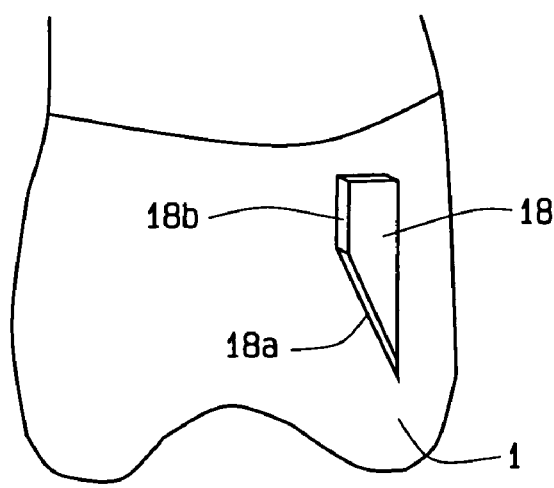
FIG. 10C illustrates a vector modifier for a tooth.

FIG. 10C illustrates a vector modifier 18. Surface 18a, here shown at an angle, functions as a seating guide and force applicator compressor. While seating the appliance surface 18a guides it into place while compressing the force applicator and distending the lateral walls of the shell or appliance, thus creating the force that induces rotation. Edge 18b receives the force 6 from the force applicators 16.

Figure 11:
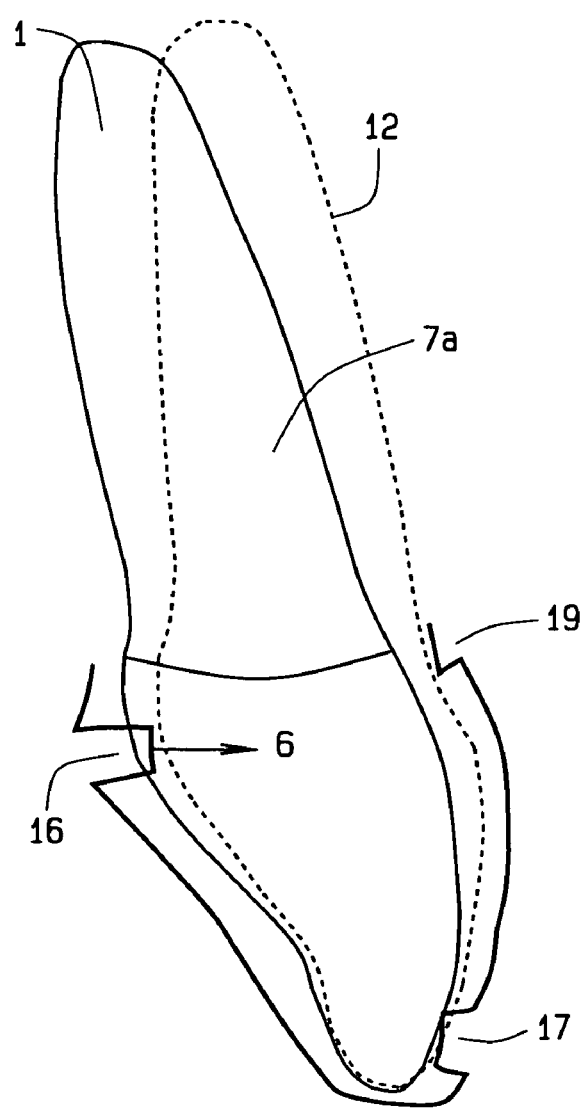
FIG. 11 discloses the application of various types of force applicators, force couplers and decouplers, to achieve corrective rotation and translation on opposing surfaces of a tooth to attain its proper alignment.

To program the amount of corrective rotation created by the force applicators and force couplers and to create a clinical guide for the treating doctor, decouplers 19, placed on the surface of the tooth, oppose the force applicators 16 where needed. FIG. 11 illustrates one embodiment of applying decouplers. Tooth 1 rotates around the fulcrum created by contact with the force couplers 17 from the equal and opposite force generated by the force 6 applied by the force applicator 16 as shown previously in FIG. 8A, 8B, 8C. The gingival portion 1a of the tooth contacts the decouplers 19 as the tooth approaches its targeted position 12. The appliance distorts in the vicinity of the decouplers 19 under the continued presence of the force applicator 16. When the moment 5 applied by the force applicators 16 equals the combined moments of the force couplers 17 and the decouplers 19, the rotation and translation stops at the programmed position. At this force balance point, the moment generated by the force applicators 16 and the force couplers 17 and the decouplers 19 sums to zero as long as the force applicators 16 are located vertically between the force couplers 17 and the decouplers 19. Although these examples present one simple movement, the examples may represent one stage of movement within a multiple stage treatment path depending on the intended outcome with many teeth simultaneously affected.

The micro-regional force application greatly improves the control of the orthodontic movement of teeth in all six degrees of freedom using elastic repositioning appliances, polymeric shells or a series of polymeric shells. The key components of this invention are the envelope of freedom, force applicators, force couplers, counterpart coupling, vector modifiers, seating guides, decouplers, and force balance points. This invention also has computer aided finite element analysis that determines the center of resistance and the center of rotation for each tooth to be moved along the calculated and predicted path of movement. The center of resistance and the center of rotation are determined from variables including but not limited to root length, roto surface area, root shape, force position, and bone height. The combination of the application of micro-regional forces and an improved movement model greatly increased the clinical control available to the treating doctor. The quality of the orthodontic treatment directly relates to the degree of control for tooth translation and rotations available to the doctor. Improved control in elastic repositioning appliances, polymeric shells, or a series of polymeric shells, vastly improves treatment quality.

Variations or modifications to the subject matter of this invention may occur to those skilled in the art upon review of the development as described herein. Such variations, if within the spirit of this development, are intended to be encompassed within the scope of the invention as shown and described. The depiction of the preferred embodiment, and as shown in the drawings, is set forth for illustrative purposes only.

I claim:

1. An orthodontic appliance for translating and rotating at least one tooth having a root within a gum and a gum line separating the root from the visible portion of a tooth, comprising;
   at least one shell, fitting over at least one tooth on at least two sides above the gum line;
   said shell having at least two of said applicators located integrally upon the interior of said shell and contacting the same side of the perimeter of the tooth and at least two of said couplers located integrally upon the interior of said shell opposite said applicator and contacting the opposite side of the perimeter of the tooth;
   each of said applicators protruding generally parallel to the gum line inwards from said shell and adapting to contact the tooth at a point of minimum surface area, each of said applicators distending said shell away from the tooth leaving a gap between the tooth and said shell, said gap extending completely around the tooth;
   each of said couplers protruding generally parallel to the gum line inwards from said shell in opposition to said applicator and adapting to contact the tooth at a point of minimum surface area, each of said couplers producing a force and moment to cooperate with movement of the tooth induced by said applicators; and,
   one of said applicators and one of said couplers locating opposite said applicator and rotating at least one tooth about any spatial axis for a limited amount of rotation with a desired moment;
   thus at least one tooth meets a goal of an orthodontic plan.

2. The orthodontic appliance of claim 1 further comprising:
   one of said applicators and one of said couplers being mutually parallel and spaced apart upon the perimeter of the tooth and locating opposite said applicator thereby rotating at least one tooth without translation.

3. The orthodontic appliance of claim 1 further comprising:
   at least one decoupler, locating proximate the gum line and opposite said applicator on the same side of said appliance as said at least one coupler, said decoupler adapting to contact a tooth at a point of minimum surface area and limiting rotation of at least one tooth a certain amount once the tooth reaches an orthodontic goal.

4. The orthodontic appliance of claim 1 further comprising:
   said shell having a lingual surface and an opposite buccal surface
   at least two of said applicators being mutually parallel upon the perimeter of the tooth and locating diagonally upon said lingual surface and said buccal surface thereby rotating the at least one tooth axially.

5. The orthodontic appliance of claim 4, further comprising:
   said applicators locating mesial distally opposite an intended direction of movement plane buccal and lingually; and,
   said couplers locating mesial distally to receive said tooth during movement thereof buccal and lingually thus producing a planned translation and controlled rotation of said tooth.

6. The orthodontic appliance of claim 4 further comprising:
   at least one modifier adapting to bond to the at least one tooth, said modifier having a planar shape with a flat edge perpendicular to one of said applicators and to one of said couplers, one of said applicators and one of said couplers pressing upon said modifier and rotating the at least one tooth incrementally either about the tooth's longitudinal axis or about an axis perpendicular to the jawbone.

7. The orthodontic appliance of claim 6 further comprising:
   a plurality of said modifiers adapting to bond to the tooth inducing a progressive rotation of the tooth by a series of said appliances.

8. An orthodontic appliance for translating and rotating at least one tooth having a root within a gum and a gum line separating the root from the visible portion of a tooth, comprising;
   at least one shell, fitting over at least one tooth on at least two sides above the gum line;
   said shell having at least two applicators located integrally upon the interior of said shell, each of said applicators mutually spaced apart upon the perimeter of the tooth and contacting the same side of the tooth and at least two couplers located integrally upon the interior of said shell opposite said applicator, each of said couplers mutually spaced apart upon the perimeter of the tooth and contacting the opposite side of the tooth;

each of said applicators protruding generally parallel to the gum line inwards from said shell and adapting to contact the tooth at a point of minimum surface area, each of said applicators distending said shell away from the tooth leaving a gap between the tooth and said shell, said gap extending completely around the tooth;

each of said couplers protruding generally parallel to the gum line inwards from said shell in opposition to said applicator and adapting to contact the tooth at a point of minimum surface area, each of said couplers producing a force and moment to cooperate with movement of the tooth induced by one of said applicators; and, each of said applicators and each of said couplers being mutually parallel and spaced apart upon the perimeter of the tooth and one of said couplers locating opposite one of said applicators thereby rotating at least one tooth without translation;

thus at least one tooth meets a goal of an orthodontic plan.

9. An orthodontic appliance for translating and rotating at least one tooth having a root within a gum and a gum line separating the root from the visible portion of a tooth, comprising;

at least one shell, fitting over at least one tooth on at least two sides above the gum line;

said shell having at least two applicators located integrally upon the interior of said shell, each of said applicators mutually spaced apart upon the perimeter of the tooth and contacting the same side of the tooth, at least two couplers located integrally upon the interior of said shell opposite said applicator, each of said couplers mutually spaced apart upon the perimeter of the tooth and contacting the opposite side of the tooth, and at least two decouplers;

each of said applicators protruding generally parallel to the gum line inwards from said shell and adapting to contact the tooth at a point of minimum surface area, said applicator distending said shell away from the tooth leaving a gap between the tooth and said shell, said gap extending completely around the tooth;

each of said couplers protruding generally parallel to the gum line inwards from said shell in opposition to said applicator and adapting to contact the tooth at a point of minimum surface area, said coupler producing a force and moment to cooperate with movement of the tooth induced by said applicator; and, at least one decoupler locating proximate the gum line and opposite one of said applicators on the same side of said appliance as one of said couplers, each of said at least one decoupler adapting to contact a tooth at a point of minimum surface area and limiting rotation of at least one tooth a certain amount;

thus at least one tooth meets a goal of an orthodontic plan.

* * * * *